US00PP24587P3

(12) United States Plant Patent
Schäfer

(10) Patent No.: US PP24,587 P3
(45) Date of Patent: Jul. 1, 2014

(54) VARIETY OF BASIL PLANT NAMED 'AJAKA'

(50) Latin Name: *Ocimum basilicum*
Varietal Denomination: Ajaka

(75) Inventor: Udo Schäfer, Wolsier (DE)

(73) Assignee: Herbalea, Grolsheim (DE)

( * ) Notice: Subject to any disclaimer, the term of this patent is extended or adjusted under 35 U.S.C. 154(b) by 149 days.

(21) Appl. No.: 13/385,808

(22) Filed: Mar. 7, 2012

(65) Prior Publication Data

US 2013/0239273 P1 Sep. 12, 2013

(51) Int. Cl.
*A01H 5/00* (2006.01)
*A01H 5/02* (2006.01)

(52) U.S. Cl.
CPC ..... *A01H 5/02* (2013.01)
USPC ..... Plt./258

(58) Field of Classification Search
CPC ..... A01G 31/06; C07C 67/08
USPC ..... Plt./258
See application file for complete search history.

(56) References Cited

PUBLICATIONS

PLUTO QZ UPOV PLUTO 201303 Citation for 'Ajaka'.*

* cited by examiner

*Primary Examiner* — Wendy C Haas
(74) *Attorney, Agent, or Firm* — The Webb Law Firm

(57) ABSTRACT

'Ajaka' is a new variety of basil plant having tolerance to low temperatures, a spicy taste, and reddish purple-colored flowers.

7 Drawing Sheets

CROSS REFERENCE TO RELATED APPLICATIONS

The new variety was discovered in the same cultivated area as basil plants named 'Dark Lady', 'Green Ball', 'Green Fortune', 'Habana', and 'Wild Magic', each respectively claimed in U.S. Plant patent application Ser. Nos. 13/385,798, 13/385,809, 13/385,811, 13/385,806, and 13/385,805.

Botanical classification: *Ocimum basilicum.*

Varietal denomination: 'AJAKA'.

BACKGROUND OF THE NEW PLANT

The present invention comprises a new and distinct cultivar of basil plant, botanically known as *Ocimum basilicum* and hereinafter referred to by the cultivar name 'Ajaka'.

The new variety was discovered and selected by the breeder in a cultivated environment in July of 2009 in Wolsier, Germany (located in the region of Brandenburg) as a naturally occurring open-pollinated new variety in a population of unpatented and unnamed *Ocimum basilicum* plants. Subsequently, the new variety was asexually reproduced by cuttings in Wolsier, Germany in 2010. Further asexual reproductions at the same location has demonstrated that the combination of characteristics as herein disclosed for the new cultivar are retained and reproduced true to type through successive generations of asexual reproduction.

The following observations, measurements and comparisons describe 8-week-old plants grown in an open field with full sun, watered as needed, and receiving weekly fertilization treatments accented with nitrogen in Wolsier, Germany. The plants were exposed to daytime temperatures of 20-30° C., and evening temperatures of 10-20° C. Color observations were taken under natural light, and the color references are made to The R.H.S. Colour Chart of The Royal Horticulture Society of London, except where general color terms of ordinary significance are used.

The present invention has not been evaluated under all possible environmental conditions. The phenotype may vary with variation in environment without a change in the genotype of the plant.

The following traits have been repeatedly observed and determined to basic characteristics of 'Ajaka' which, in combination, distinguish this basil plant as a new and distinct cultivar:

1. Tall and well-branched plant habit;
2. Sweet-spicy fragrance;
3. Spicy tasting;
4. Tolerant to *Fusarium, Botrytis*, and *Pythium*; and
5. Low temperature tolerance.

Further, the new variety exhibits a tall and well-branched habit like basil variety 'Dark Lady' (U.S. Plant patent application Ser. No. 13/385,798). However, 'Dark Lady' has very dark violet leaves and an aromatic fragrance, while 'Ajaka' has green leaves and a sweet-spicy fragrance. The following Table 1 provides a further comparative listing of botanical characteristics of 'Ajaka' and 'Dark Lady'.

TABLE 1

| Botanical characteristics | 'Ajaka' | 'Dark Lady' |
|---|---|---|
| Height from soil to top of plant: | 60 cm. | 50 cm. |
| Leaf length: | 5 cm. | 4.5 cm. |
| Number of flowers per plant: | About 150 | About 200 |
| Flower longevity: | 4-6 weeks | 6-8 weeks |

BRIEF DESCRIPTION OF THE DRAWINGS

The accompanying photographic drawings illustrate the new variety, with the colors being as nearly true as is possible with color illustrations of this type.

DESCRIPTION OF THE PLANT

Figure 1:
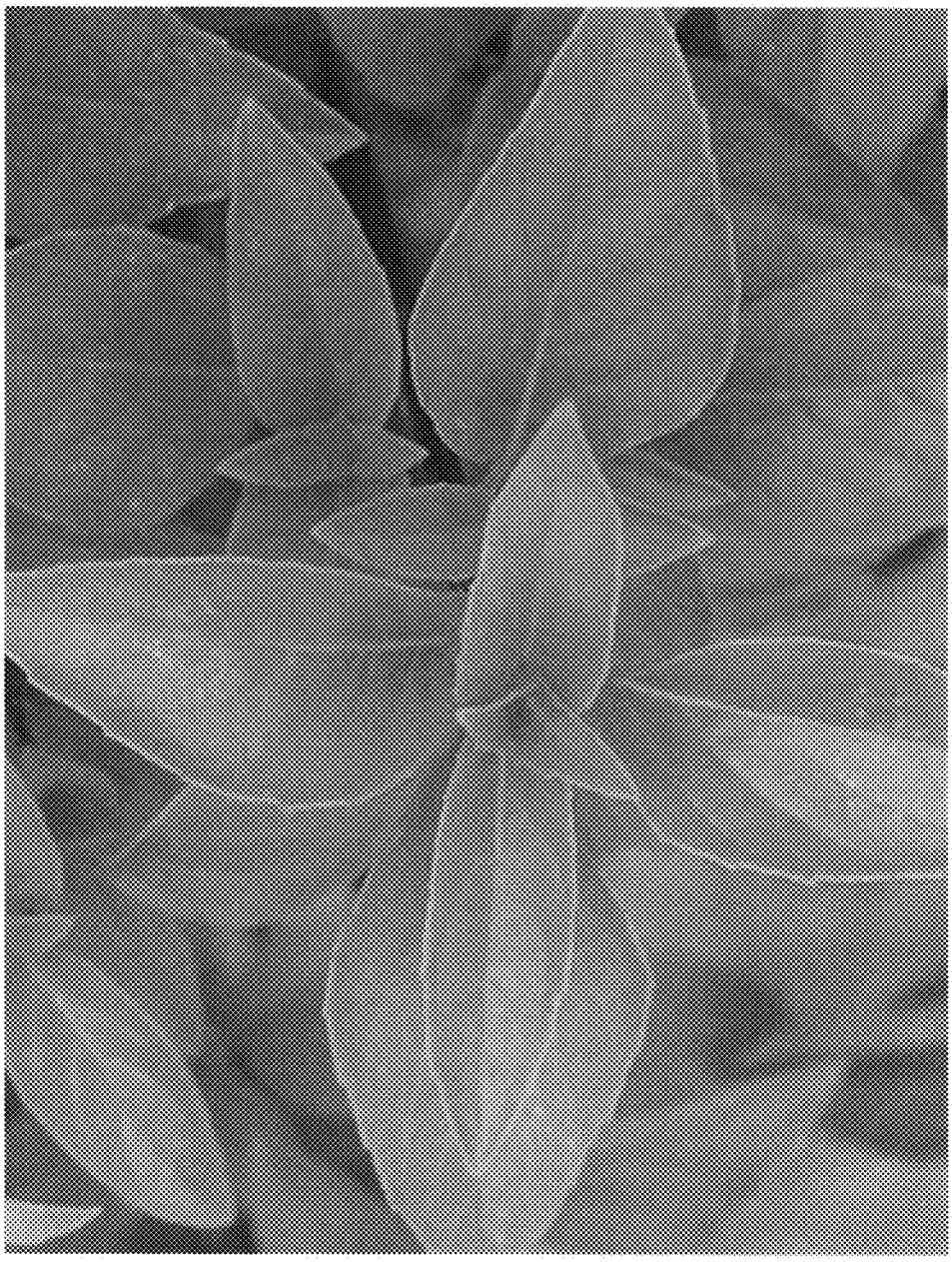
FIG. 1 is a close-up photograph of the leaves of the new variety.
Figure 2:
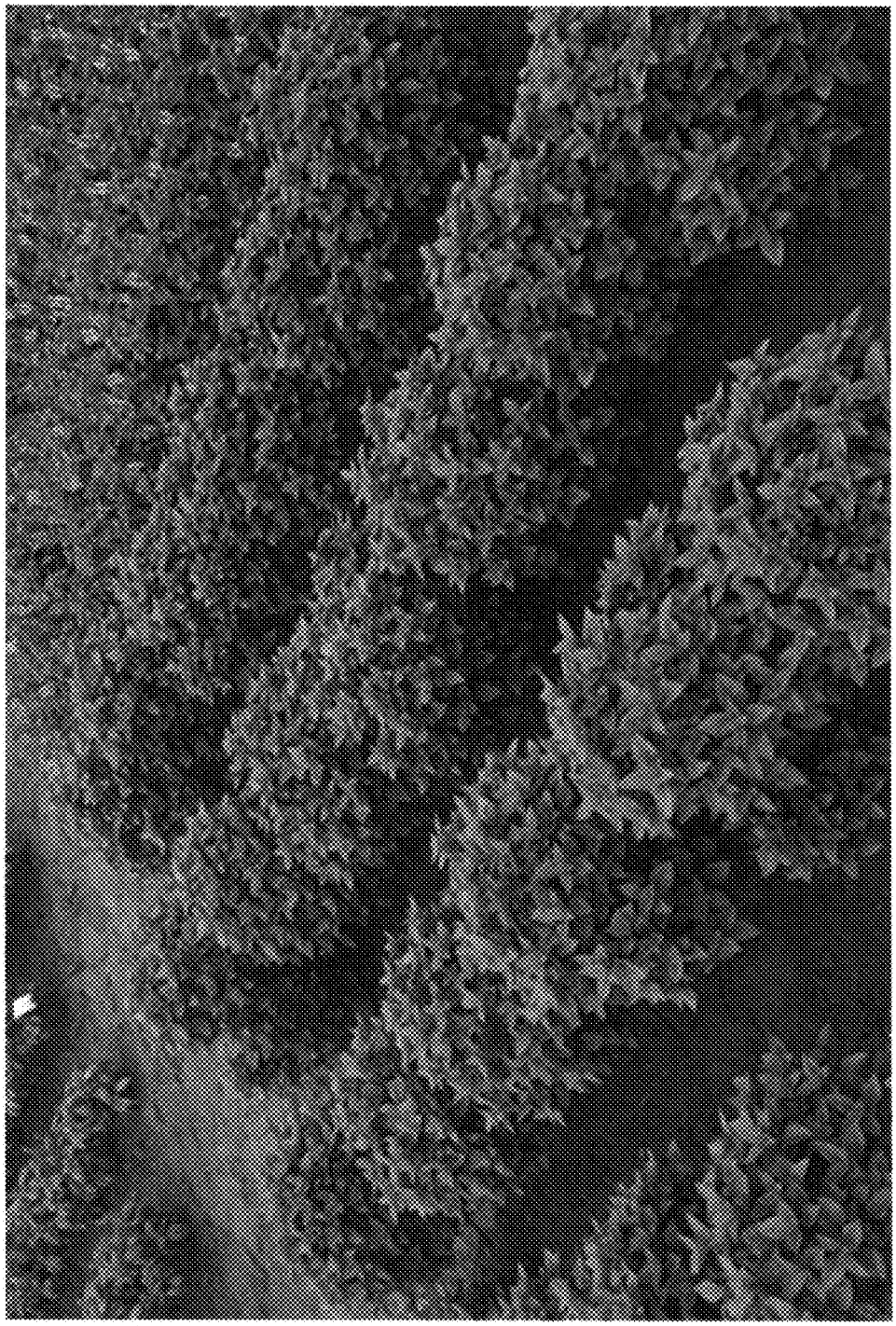
FIG. 2 is a photograph of a field of plants of the new variety.
Figure 3:
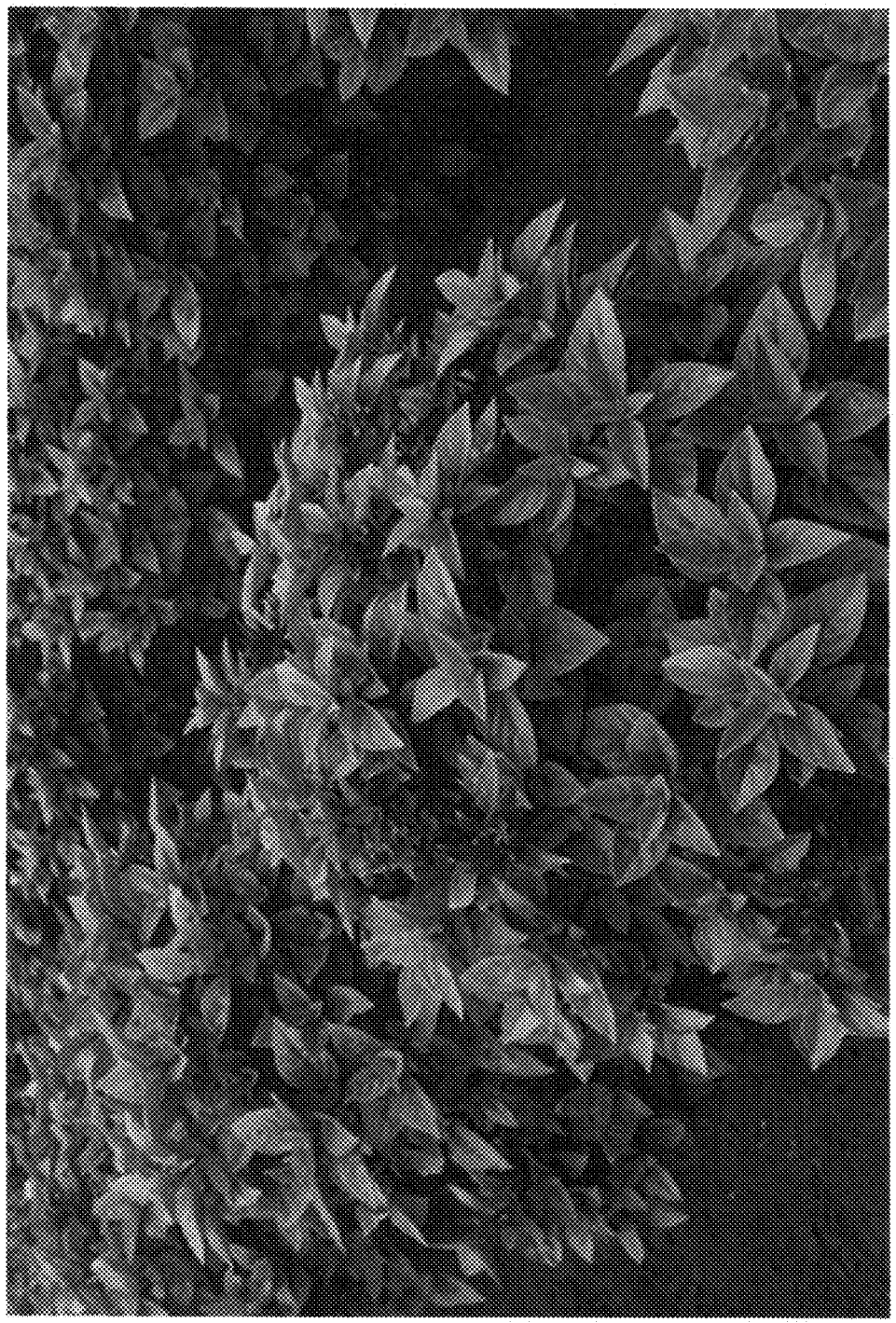
FIG. 3 is a photograph of multiple plants of the new variety.
Figure 4:
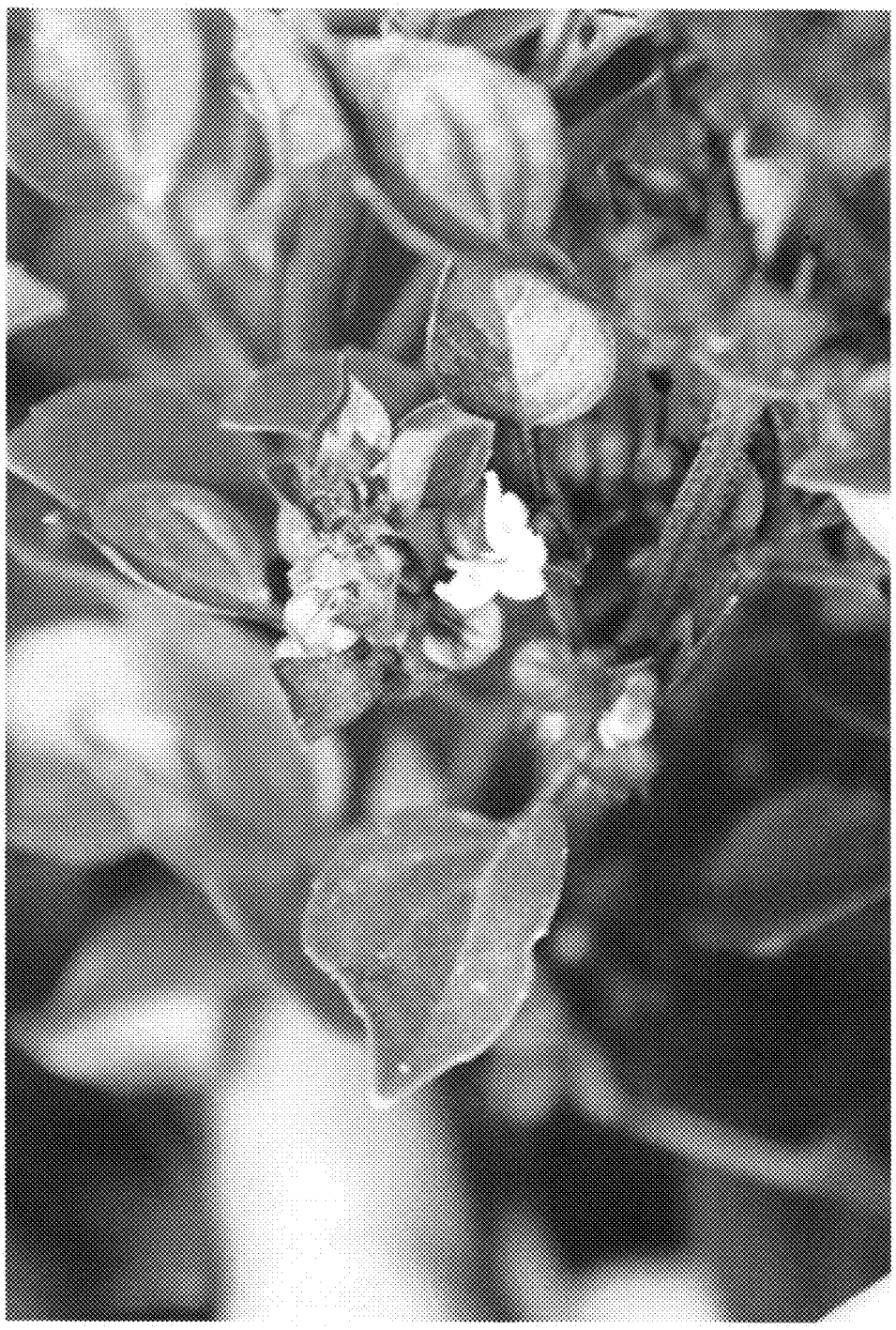
FIG. 4 is a close-up photograph of the flowers of the new variety.
Figure 5:
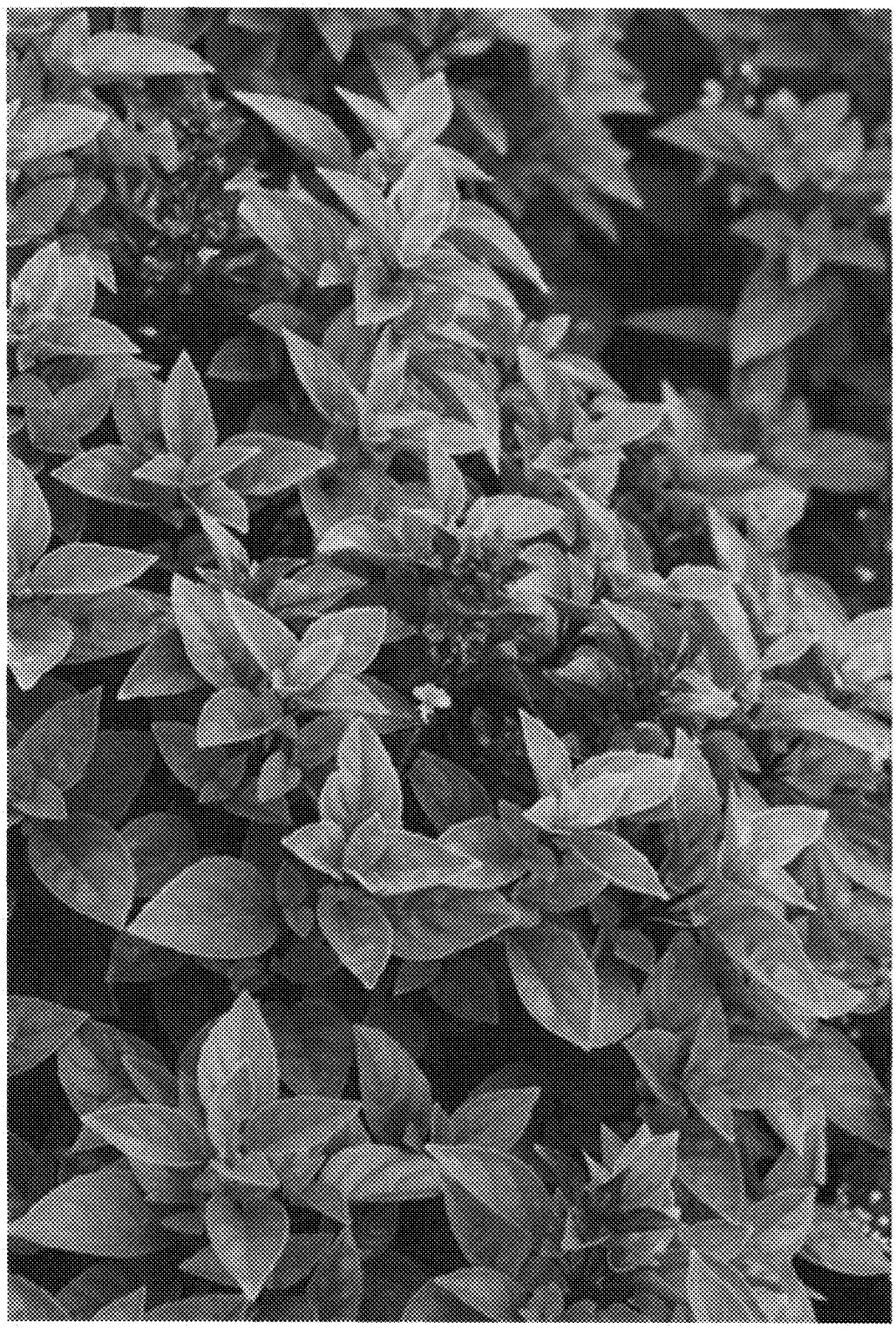
FIG. 5 is a photograph of multiple blooming plants of the new variety.
Figure 6:
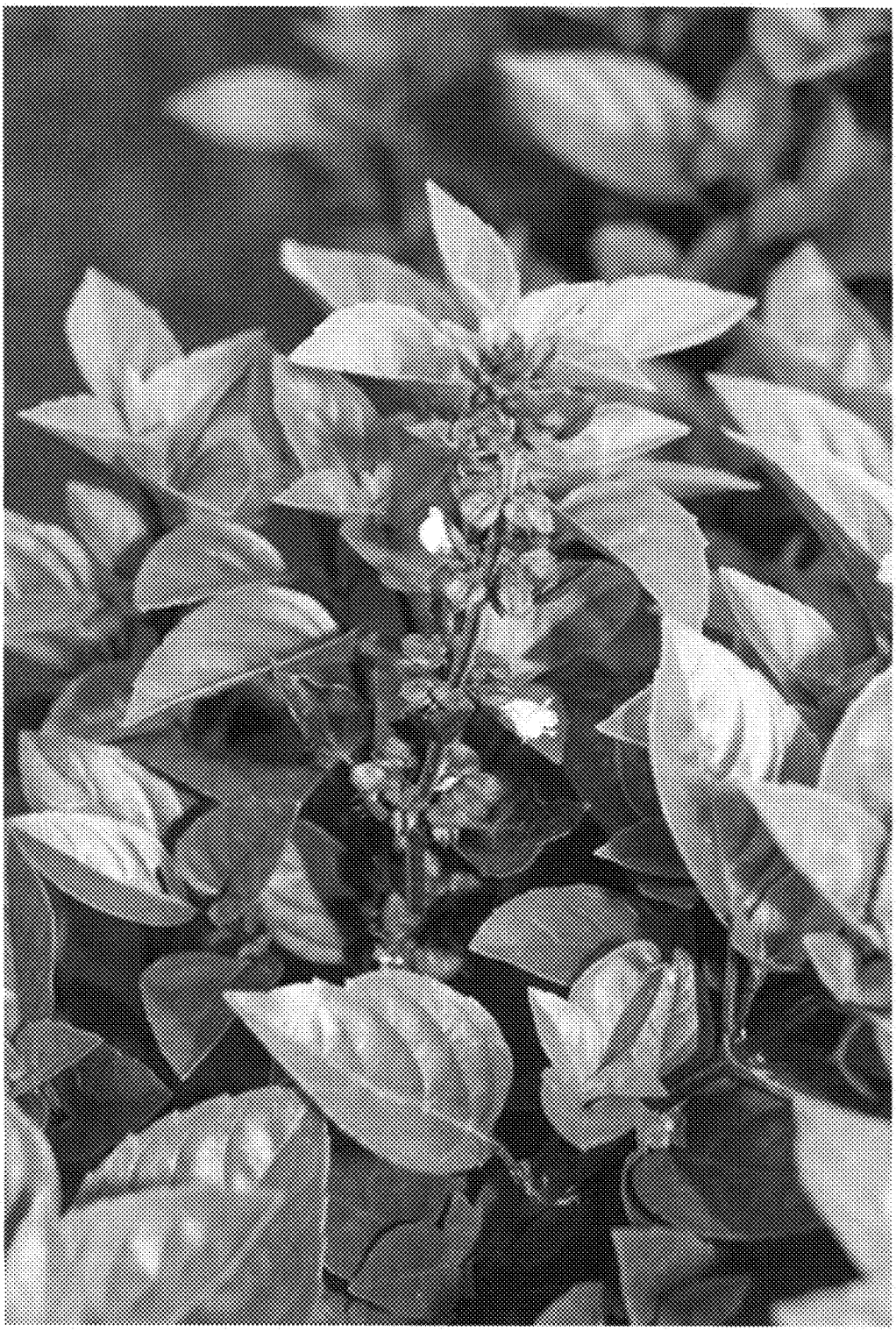
FIG. 6 is close-up photograph of a blooming plant of the new variety.
Figure 7:
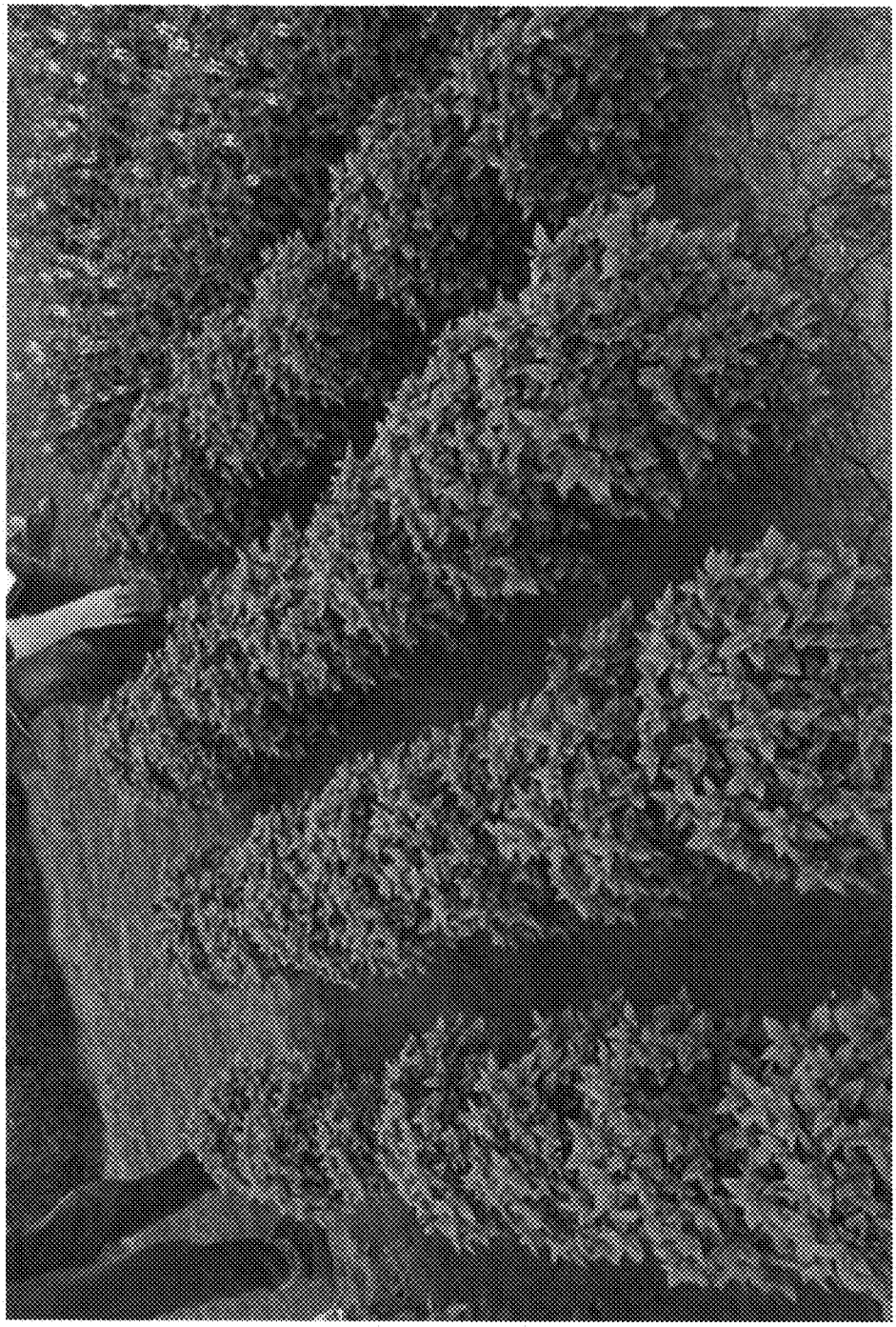
FIG. 7 is a photograph of a field of plants of the new variety.

Time to initiate roots: 5 days at 22° C.

Time to produce a rooted plant: 9 days at 22° C.

Root description: Finely branched white roots with a fibrous habit.

Form: Erect.

Height from soil to top of plant: 60 cm.

Plant diameter: 40 cm.

Growth habit: Erect and loose with a low-branching habit.

Vigor: Strong, when compared to 'Wild Magic' (U.S. Plant application Ser. No. 13/385,805) and 'Green Ball' (U.S. Plant patent application Ser. No. 13/385,809).

Main stem:

*Length.*—60 cm.

*Width.*—0.5 cm.

*Color.*—Purple Group RHS N77D to Violet Group RHS 83A.

*Number of branches.*—10-20.

*Node spacing.*—5 cm.

Leaves:

*Arrangement.*—Decussate; pinnate.

*Number of leaves per plant.*—About 400.

*Length.*—5 cm.

*Width.*—4 cm.

*Shape of leaf (generally).*—Elliptic.

*Shape of apex.*—Apiculate.

*Shape of base.*—Elliptic.

*Texture.*—The veins are nicely visible; the structure does not stand out particularly, except the centerline. No pubescence is present.

*Aspect.*—Upwards.

*Margin type.*—Shallow serration present.

*Upper surface color.*—Green Group RHS 137C.

*Lower surface color.*—Green Group RHS 137C.

*Veins.*—Upper surface description and color: Pinnate; Yellow-Green Group RHS 146C. Lower surface description and color: Pinnate; Green Group RHS 139C.

*Petiole.*—Length: 1-3 cm. Diameter: 2 mm. Color: Green Group RHS 137A to Yellow-Green Group RHS 146C. Texture: Smooth. Shape: Round.

Reproductive organs: 1 pistil and 4 stamens present.

Flowers:

*Natural flowering season.*—End of June through September in the Brandenburg Region of Germany.

*Number of flowers per plant.*—About 150.

*Fragrance.*—Aromatic.

*Longevity.*—4-6 weeks.

*Flower type.*—Labiate.

*Flower height.*—0.7 cm.

*Flower diameter.*—0.5 cm.

*Petal color.*—Upper surface: Red-Purple Group RHS N74C. Lower surface: Red-Purple Group RHS 69C.

Seed description: Sterile.

Disease/pest resistance: Tolerant to *Fusarium oxysporum.*

Weather tolerance: Very tolerant to rain and cold nights (down to 8° C.).

Harvesting season: Early summer to fall outdoors; year round indoors.

Flavor: Sweet-spicy.

Aroma: Spicy.

Essential oils: Linalool-eugenol-type.

Productivity/yield per acre:

*Fresh.*—7 tons per acre.

*Dried.*—1 ton per acre.

Average life span: 5 months.

Use: Multiple uses. The new variety can be used as a pot plant, ornamental plant, culinary herb, or fresh and dried herb.

Fresh shelf life: Over 1 week under cool conditions (5-8° C.).

I claim:

1. A new and distinct variety of basil plant named 'Ajaka' as herein described and illustrated.

* * * * *

UNITED STATES PATENT AND TRADEMARK OFFICE

CERTIFICATE OF CORRECTION

PATENT NO. : PP24,587 P3
APPLICATION NO. : 13/385808
DATED : July 1, 2014
INVENTOR(S) : Udo Schäfer It is certified that error appears in the above-identified patent and that said Letters Patent is hereby corrected as shown below:

On the Title Page

Item (73) Assignee, "Herbalea," should read -- Herbalea GmbH, --

In the Specification

Column 2, Line 1, delete "to The" and insert -- to the --

Column 4, Line 33, delete "/yield" and insert -- /Yield --

Signed and Sealed this
Fourteenth Day of October, 2014

Michelle K. Lee

Michelle K. Lee
*Deputy Director of the United States Patent and Trademark Office*